US005851986A

United States Patent [19]

Takada et al.

[11] Patent Number: 5,851,986

[45] Date of Patent: Dec. 22, 1998

[54] PROMOTING BONE FORMATION AND INHIBITING BONE RESORPTION WITH HIGH MOBILITY GROUP PROTEIN-1 (HMG-1)

[75] Inventors: Yukihiro Takada; Junichi Yamamura, both of Kawagoe; Masaaki Goto, Ishibashimachi; Seiichiro Aoe, Sayama, all of Japan

[73] Assignee: Snow Brand Milk Products Co., Ltd., Japan

[21] Appl. No.: 803,545

[22] Filed: Feb. 20, 1997

[30] Foreign Application Priority Data

Feb. 23, 1996 [JP] Japan .................................... 8-061987

[51] Int. Cl.[6] .......................... A01N 37/18; A61K 31/70; A61K 35/20; A61K 35/55

[52] U.S. Cl. ................................ 514/2; 514/21; 424/535; 424/568

[58] Field of Search ..................... 514/2, 4, 21; 424/535, 424/520, 568

[56] References Cited

U.S. PATENT DOCUMENTS 5,654,019 8/1997 Kobayashi et al. ....................... 426/41

FOREIGN PATENT DOCUMENTS 4016165 1/1992 Japan .
404183371 6/1992 Japan .

OTHER PUBLICATIONS

Parris et al., “Thermal Stability of Whey Protein Concentrate Mixtures: Aggregate Formation,” J. Dairy Sci. (1997) 80: 19–28, 1997.

Merenmies et al., “30–kDa heparin–binding protein of brain (amphoterin) inveolved in neurite outgrowth”, J. Biol. Chem. (1991) 266(25): 16722–729.

Shirakawa et al., “Primary Structure of non–histone protein HMG1 revealed by the nucleotide sequence”, Biochem. (1988) 27: 6159–63, 1990.

Shakoori et al. “Differential expression of the chromosomal high mobility group proteins 14 and 17 during the onset of diffeentiation in mammalian osteoblasts and promyelocytic leukemia cells”, J. Cell. Biochem. (1993) 51: 479–487, 1993.

Wen et al. “A human placental cDNA clone that encodes nonhistone chromosomal protein HMG–1”, Nucleic Acids Res. (1989) 17(3): 1197–1214, 1989.

Stros et al. “Calcium binding to HMG1 protein induces DNA looping by the HMG–box domains”, FEBS Lett. (1994) 344: 201–206, 1994.

Abdul–Razzak et al. “Isolation and characterization of folded fragments released by Staphylcoccal aures proteinase from the non–histone chromosomal protein HMG–1”, Biochem. Biophys, Acta (1989) 996: 125–131, 1989.

Tomita et al. “Direct in vivo gene introduction into rat kidney”, (1992) 186(1): 129–134, 1992.

Tsuda et al. “Primary structure of non–histone protein HMG1 by the nucleotide sequence”, Biochemistry (1988) 27: 6159–6163, 1988.

*Primary Examiner*—Jon P. Weber
*Assistant Examiner*—Susan Harley
*Attorney, Agent, or Firm*—Testa Hurwitz & Thibeault, LLP

[57] ABSTRACT

A method for promoting osteoblast proliferation or inhibiting bone resorption comprising administering to a subject in need thereof, a composition comprising High Mobility Group Protein (HMG-1) is disclosed.

2 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 30 amino acids
( B ) TYPE: amino acid
( C ) STRANDEDNESS:
( D ) TOPOLOGY: linear ( i i ) MOLECULE TYPE: peptide -continued ( x i ) SEQUENCE DESCRIPTION: SEQ ID NO:1:

```
Gly Lys Gly Asp Pro Lys Lys Pro Arg Gly Lys Met Ser Ser Tyr Ala
 1              5                   10                  15

Phe Phe Val Gln Thr Cys Arg Glu Glu His Lys Lys Lys His
            20                  25                  30
```

PROMOTING BONE FORMATION AND INHIBITING BONE RESORPTION WITH HIGH MOBILITY GROUP PROTEIN-1 (HMG-1)

FIELD OF THE INVENTION

The present invention relates to an agent capable of promoting bone formation and inhibiting bone resorption, comprising a protein having a specific N-terminal amino acid sequence, such as HMG (high-mobility-group) protein or Amphoterin etc. or degradation products thereof, as an effective ingredient. Further, the present invention also relates to a drink, food, medicine or feed containing a protein having a specific N-terminal sequence, such as HMG protein or Amphoterin or degradation products thereof.

BACKGROUND OF THE INVENTION

Coincident with an increase in the human life span, is the recent increase in the incidence of metabolic bone diseases such as osteoporosis, bone fracture and bone pain. Bone tissue, bone formation and bone resorption are continuously taking place. Though the balance of bone formation and bone resorption takes place in one's youth, bone resorption exceeds bone formation due to various causes as one ages ("uncoupling"). Prolonged bone resorption causes bone tissue to become fragile, resulting in metabolic bone diseases such as osteoporosis, bone fracture, and bone pain, etc.

Conventional methods of preventing or treating metabolic bone diseases by inhibiting uncoupling include, (1) dietary calcium supplementation, (2) light exercise, (3) sunbathing, and (4) medicinal therapy. Calcium supplements include calcium salts such as calcium carbonate, calcium phosphate, etc., and naturally occurring calcium-containing preparations such as bovine bone powder, egg shell, fish bone powder, etc. They are, however, not necessarily suitable for oral administration. Light exercise, jogging or walking are also recommended. However, these activities are troublesome to a person who has become weak or to an immobilized elderly person. Sunbathing is believed to be an effective means for supplementing the active form of vitamin $D_3$ but is not sufficient as a therapy. A medicinal therapy, such as 1 $\alpha$-hydroxyvitamin $D_3$ and/or calcitonin, may be used as an effective treatment for osteoporosis. However, these compounds are medicines and can not be used as food supplements.

The present inventors have discovered a factor, present in whey proteins, that strengthens bone and inhibits bone resorption. We discovered a protein and a peptide mixture having bone strengthening activity obtained by removing salt from the water soluble fraction of whey protein using a reverse osmotic membrane and/or electrophoresis. (Japanese published unexamined patent application No. 183371/1992). Further, we found that a fraction derived from this protein or peptide mixture by ethanol treatment, heating, addition of salt and ultrafiltration treatment promoted osteoblast proliferation and strengthened bone (Japanese published patent application No. 176715/1993, Japanese published patent application 320066/1993). In addition, we also found that a basic protein present at very low levels in milk promoted osteoblast proliferation, strengthened bone and inhibited bone resorption (Japanese patent application No. 207509/1995). The present inventors have isolated and purified an active milk component capable of promoting osteoblast proliferation and inhibiting bone resorption. We have isolated and purified this component and have identified is as HMG protein or Amphoterin. These proteins are found not only in milk but also in mammalian thymus, and brain, etc., and are distributed widely throughout the body. We also found that HMG protein and Amphoterin isolated from the above tissue had the same activity as that isolated from milk. Further, the degradation products of HMG protein and Amphoterin retain this activity. Since the N-terminal amino acid sequence of these HMG proteins and Amphoterins is the same (Bioscience Reports, vol. 4, pp. 49–57, 1984, and J. Biol. Chem., vol. 226, pp 16722–16729, 1991), it is expected that other proteins having this N-terminal amino acid sequence have similar bone reinforcing activities.

SUMMARY OF THE INVENTION

Accordingly, an object of the present invention is to provide an agent that promotes bone formation and inhibits bone resorption, comprising whole protein and/or degradation products thereof whose amino acid sequence at the N-terminus is Gly-Lys-Gly-Asp-Pro-Lys-Lys-Pro-Arg-Gly-Lys-Met-Ser-Ser-Tyr-Ala-Phe-Phe-Val-Gln-Thr-Cys-Arg-Glu-Glu-His-Lys-Lys-Lys-His (SEQ ID NO: 1). Another object of the present invention is to provide a drink, food, medicine or feed containing whole protein and/or degradation products thereof whose amino acid sequence at the N-terminus is Gly-Lys-Gly-Asp-Pro-Lys-Lys-Pro-Arg-Gly-Lys-Met-Ser-Ser-Tyr-Ala-Phe-Phe-Val-Gln-Thr-Cys-Arg-Glu-Glu-His-Lys-Lys-Lys-His (SEQ ID NO: 1).

DETAILED DESCRIPTION OF THE INVENTION

The present invention provides as an effective ingredient an agent that promotes bone formation and inhibits bone resorption, and has the following common amino acid sequence at the N-terminus thereof;

Gly-Lys-Gly-Asp-Pro-Lys-Lys-Pro-Arg-Gly-Lys-Met-Ser-Ser-Tyr-Ala-Phe-Phe-Val-Gln-Thr-Cys-Arg-Glu-Glu-His-Lys-Lys-Lys-His-(SEQ ID NO: 1).

Such proteins include HMG protein and Amphoterin and have the same N-terminal amino acid sequence regardless of the origin thereof. In the present invention, degradation products thereof can also be used as effective ingredients.

HMG Protein is a non-histone protein and comprises a large amount of basic amino acids and acidic amino acids. HMG has a basic N-terminus and an acidic C-terminus, which is non-symmetrical. The binding modality between HMG protein and DNA is ionic. It is known that there is an interaction between basic amino acids and phosphate groups of DNA. HMG protein has been found in all tissues of higher class biological organisms so far and is known to share similarity with histone protein (Kaplan, D. J., Duncan, C. H., Nucleic Acid Res., vol. 16, p. 10375, 1988).

HMG protein can be obtained from skim milk derived from cow, human, goat and sheep milk, etc. Such treatment regimes include heating, the addition of salt, ethanol precipitation, ion exchange, chromatography, gel filtration chromatography, other kinds of chromatography and ultrafiltration etc.

Alternatively, Amphoterin which is also an effective ingredient of the present invention, is a 30 kDa of heparin binding protein and which binds strongly with cells of the neural system. Amphoterin is also thought to play a role in cell adhesion and/or formation of dendrites and to play an important role in the development of the brain.

Amphoterin can be obtained, like HMG protein, from skim milk isolated from cow, human, goat and sheep milk, etc. Such treatments include heating, the addition of salt, ethanol precipitation, ion exchange chromatography, gel filtration chromatography, other kinds of chromatography and ultrafiltration etc.

The degradation products of HMG protein and Amphoterin which are effective ingredients of the present invention comprise a peptide mixture obtained by degradation of HMG protein or Amphoterin with trypsin, chymotrypsin, pepsin, papain, kalikrein, cathepsin, thermolysin and V8 protease etc. The peptide fragments thereby derived have a molecular weight of 100 Da–20,000 Da by HPLC gel filtration chromatography.

The agent that promotes bone formation and inhibits bone resorption comprises a protein having a specific N-terminus, such as that of HMG protein or Amphoterin, or degradation products thereof as an effective ingredient. The protein having a specific N-terminus, or degradation products thereof, can be combined with a drink or food, such as milk, milk drinks, coffee drinks, juice, jelly, crackers, bread, noodle or sausage etc., or can be used as a medicine in the form of tablets, or powders, etc. Further, by combining the effective ingredient with a calcium agent, such as calcium chloride, calcium carbonate, calcium lactate, egg shell, and calcium derived from milk, etc., the activity of the effective ingredient for promoting bone formation can be augmented.

The agent promoting bone formation and inhibiting bone resorption can be taken at a dosage of 100 ng–10 mg per day, several times per day, for an adult. By taking the agent promoting bone formation and inhibiting bone resorption, metabolic bone diseases such as osteoporosis can thereby be prevented or the condition improved.

Alternatively, these effective ingredients can be combined with feeds so that bone formation can be promoted and/or bone resorption can be inhibited in livestock or poultry.

As described above, the agent promoting bone formation or inhibiting bone resorption of the present invention comprising protein having a specific N-terminal amino acid sequence or degradation products thereof, such as HMG protein or Amphoterin, as an effective ingredient can be used to prevent and/or improve various kinds of bone metabolic diseases such as osteoporosis. Further, foods, drinks, medicines or feeds comprising these proteins or degradation products thereof can prevent and/or improve these bone metabolic diseases in the same manner as the above.

The present invention is further understood by the following examples and test examples. However, the scope of the present invention is not limited thereto.

EXAMPLE 1

A column packed with sulfonated Chitopearl (Fujiboseki) was washed with deionized water and with a sufficient volume of cationized water. 300 1 of skim milk was applied to the cation exchange resin and the resin was washed sufficiently with deionized water. Basic protein adsorbed thereto was eluted with a linear gradient of 0.1–1M NaCl in 0.02M carbonate buffer solution and recovered. The eluted fraction comprising HMG protein was then loaded onto an S-Sepharose column equilibrated with 0.1M phosphate buffer solution (pH 6.5) and eluted with a linear gradient of 0.1–1.0M NaCl. The fraction obtained was heated at 90° C. for 10 min., centrifuged, and a precipitate removed. The fraction was then loaded on a Mono Q ion exchange column equilibrated with 0.1M phosphate buffer solution (pH 6.5) and eluted with linear gradient of 0.1–1.0M NaCl. The fraction was then loaded onto a Sepharose 12 gel filtration column and fractionated. Finally, the fraction was purified by high performance liquid chromatography using C4 reversed phase chromatography to give 135 mg of HMG-protein.

EXAMPLE 2

Preparation of HMG protein from porcine thymus was carried out according to the method of Y. Adachi (J. Chromatography, 530, 39–46 (1990).

Thymus chromatin (253 g) was homogenized in 0.35M NaCl with a potter-type homogenizer and centrifuged (5000×g, 20 min.), and dialyzed against 10 mM phosphate buffer solution (pH 7.8) overnight. The dialysate was loaded onto a PBB-94 column, equilibrated with 10 mM phosphate buffer solution (pH 7.8) and eluted with a linear gradient of 0.1–1.0M NaCl to yield 25 mg of HMG-protein.

EXAMPLE 3

Amphoterin was prepared according to the method of R. Heikki (Heikki, R., Riitta, P., J. Biol. Chem., vol. 262, pp. 16625–16635, 1987). That is, 112.7 g of brain from SD rats was homogenized in 100 ml of ice-cooled PBS (137 mM sodium chloride, 27 mM potassium chloride, 8.1 mM disodium hydrogenphosphate, 1.5 mM potassium dihydrogenphosphate, pH 7.4) and centrifuged 100,000×g for 1 hour to recover a precipitate. Then, this precipitate was dissolved in 50 mM octyl glucoside containing 1 mM PMSF (phenylmethylsulfonyl fluoride) and 5 mM EDTA, stirred for 1 hour and centrifuged 100,000×g for 1 hour to remove a precipitate. The supernatant was loaded onto a Heparin-Sepharose column and eluted with a linear gradient of 2M sodium chloride, followed by Superose 12 gel filtration chromatography and lyophilization to yield 12 mg of Amphoterin.

EXAMPLE 4

HMG protein (50 mg) obtained in example 1 was resuspended in 10 ml of water and trypsin added to a final concentration of 0.01%. Enzymatic degradation was carried out at 37° C. for 1 hour and stopped by deactivating the enzyme at 90° C. for 5 min., followed by lyophilization to yield 43 mg of HMG protein degradation product. The molecular weight range of this degradation product was 100–18,000 Da by HPLC gel filtration chromatography (Toso).

EXAMPLE 5

Amphoterin (5 mg) obtained in example 3 was resuspended in 10 ml of water and pancreatin added to a final concentration of 0.001%. Enzymatic degradation was carried out at 37° C. for 5 hours and stopped by deactivating the enzyme at 90° C. for 5 min., followed by lyophilization to yield 4.3 mg of Amphoterin degradation product. The molecular weight range of this degradation product was 200–20,000 Da by HPLC gel filtration chromatography.

TEST EXAMPLE 1

Substances obtained in examples 1–5 were examined for their ability to promote osteoblastic proliferation. That is, $2\times10^4$ cells/ml of mouse osteoblast cell line MC3T3-E1 in α-modified minimum essential medium (α-MEM) medium containing 10% bovine fetal serum (Flow laboratories) was inoculated into each well of a 96-well plate and cultured at 37° C. The medium was then changed to α-MEM which did not contain bovine fetal serum, to which a fraction obtained in examples 105 was added to a final concentration of 10 μg/ml and cultured at 37° C. for 18 hours. After 2 hours, 0.02 MBq of $^3$H-thymidine was added thereto, cells were collected on a filter paper by a cell harvester, radioactivity incorporated into the cells was counted by liquid scintillation counting to determine the presence of osteoblastic proliferative activity. A cell culture without any addition of protein fractions 1–5 were used as a control group. Proliferative activity was calculated by defining 100% as that occurring in the control culture and the results are shown in Table 1.

TABLE 1

| Fraction | Osteoblastic proliferative activity |
|---|---|
| Example 1 | 189 ± 25 (%) |
| Example 2 | 183 ± 29 |
| Example 3 | 140 ± 19 |
| Example 4 | 153 ± 15 |
| Example 5 | 143 ± 16 |

Compared to the growth of the control group, cells to which one of the substances obtained in examples 1–5 was added showed increased proliferation, demonstrating that the substances have osteoblast proliferation activity. Similar results were obtained using another osteoblast cell line UMR.

TEST EXAMPLE 2

Substances obtained in examples 1–5 were examined for their ability to inhibit action thereof on bone resorption. Long bones were extirpated from 10–20 day old ICR mice and whole bone marrow cells comprising osteoclasts were obtained by removing soft tissue from the bones and mincing the bones in a α-MEM containing 5% bovine fetal serum. About $2\times10^6$ of these cells were placed in α-MEM containing 5% bovine fetal serum and placed on a piece of dentinum. After two hours, one of test samples 105 in α-MEM containing 5% bovine fetal serum was added to the cells to a final concentration of 10 μg/ml, cultured for 5 days and bone osteoblast resorptive activity analyzed. Bone resorption was measured by removing the cells from the piece of dentinum after cultivation, staining the dentinum with Hematoxylin dye and counting the number of bone resorptive pit by morphometrical analysis with PIAS LA-555. Cells cultured on dentinum in the absence of a substance from examples 105 served as controls. Bone resorptive activity was calculated by defining 100% as that observed in the control group. The results are shown in Table 2.

TABLE 2

| Fraction | Bone resorptive activity |
|---|---|
| Example 1 | 70.7 ± 5.7 |
| Example 2 | 79.9 ± 5.7 |
| Example 3 | 77.9 ± 8.6 |
| Example 4 | 75.4 + 8.6 |
| Example 5 | 85.4 ± 8.6 |

Compared to the bone resorptive activity of the control group, any group to which a substance obtained in example 1–5 was added showed an increased inhibition of bone resorptive activity.

EXAMPLE 6

A drink that promotes bone formation and inhibits bone resorption was prepared by mixing the raw materials shown in Table 3, packing them into a container and sterilizing them by heating.

TABLE 3

| | |
|---|---|
| Mixed isomerized sugar | 15.0 (weight %) |
| Fruit juice | 10.0 |
| Citric acid | 0.5 |
| Substance obtained in example 3 | 0.0005 |
| Flavor | 0.1 |
| Calcium | 0.5 |
| Water | 73.9 |

EXAMPLE 7

A tablet that promotes bone formation and inhibits bone resorption was prepared by mixing the raw materials shown in Table 4 and formulating them under pressure

TABLE 4

| | |
|---|---|
| Crystalline glucose hydrate | 93.5 (weight %) |
| Substance obtained example 2 | 0.05 |
| Calcium | 5.0 |
| Sugar ester | 1.0 |
| Flavor | 0.5 |

EXAMPLE 8

A cracker that promotes bone formation and inhibits bone resorption was prepared by mixing the raw materials represented in Table 5, making a dough, and formulating and baking it.

TABLE 5

| | |
|---|---|
| Wheat powder | 50.0 (weight %) |
| Sugar | 20.0 |
| Sodium chloride | 0.5 |
| Margarine | 12.5 |
| Egg | 12.1 |
| Water | 3.7 |
| Sodium bicarbonate | 0.1 |
| Ammonium bicarbonate | 0.2 |

TABLE 5-continued

| | |
|---|---|
| Calcium bicarbonate | 0.1 |
| Substance obtained in example 2 | 0.005 |

EXAMPLE 9

A jelly that promotes bone formation and inhibits bone resorption was prepared by mixing the raw materials shown in Table 6, packing them into a container and sterilizing them by heating.

TABLE 6

| | |
|---|---|
| Fructose | 20.0 (weight %) |
| Granulated sugar | 15.0 |
| Miller jelly | 5.0 |
| Agar | 1.0 |
| Substance obtained in example 4 | 0.0005 |
| Flavor | 0.11 |
| Calcium | 0.1 |
| Water | 58.39 |

EXAMPLE 10

A processed cheese that promotes bone formation and inhibits bone resorption was prepared by mixing the raw materials shown in Table 7 and emulsifying them at 85° C.

TABLE 7

| | |
|---|---|
| Gouda cheese | 43.0 (weight %) |
| Cheddar cheese | 43.5 |
| Sodium citrate | 2.0 |
| Substance obtained in example 1 | 0.005 |
| Milk-derived calcium | 1.0 |
| Water | 10.5 |

EXAMPLE 11

After sterilizing (12% by weight) reducing skim milk at 90° C. for 20 min., *Lactobacillus acidophilus* and *Streptococcus thermophilus* were inoculated therein to give 2 kinds of starter cultures, which were mixed in equal volumes. A yogurt that promotes bone formation and inhibits bone resorption was prepared by mixing raw materials represented in Table 8 and fermenting them.

TABLE 8

| | |
|---|---|
| Yogurt mix | 97.0 (weight %) |
| Starter culture | 3.0 |
| Substance obtained in example 1 | 0.0005 |

EXAMPLE 12

A dry milk for infant that promotes bone formation and inhibits bone resorption was prepared by mixing the raw materials shown in Table 9.

TABLE 9

| | |
|---|---|
| Skim milk | 75.61 (weight %) |
| Whey protein condensate | 2.36 |
| Lactose | 13.86 |
| Mineral mix | 0.32 |
| Water soluble vitamin mix | 0.32 |
| Fat containing fat-soluble vitamin | 7.53 |
| Substance obtained in example 1 | 0.001 |

EXAMPLE 13

A dog feed that promotes bone formation and inhibits bone resorption was prepared by mixing the raw materials shown in Table 10.

TABLE 10

| | |
|---|---|
| Soy bean cake | 12.0 (weight %) |
| Skim milk powder | 14.0 |
| Soy bean oil | 4.0 |
| Corn oil | 2.0 |
| Palm oil | 28.0 |
| Corn starch | 15.0 |
| Wheat powder | 9.0 |
| Wheat bran | 2.0 |
| Vitamin mix | 9.0 |
| Mineral mix | 2.0 |
| Cellulose | 3.0 |
| Substance obtained in example 1 | 0.001 |

We claim:

1. A method for promoting osteoblast proliferation or inhibiting bone resorption comprising administering to a subject in need thereof, a composition comprising High Mobility Group Protein-1 (HMG-1), with the proviso that said composition is not milk, milk products or milk-containing products.

2. The method according to claim 1, wherein said composition is combined with a calcium salt.

* * * * *